US010647955B2

(12) United States Patent
Taniguchi et al.

(10) Patent No.: US 10,647,955 B2
(45) Date of Patent: May 12, 2020

(54) CELL CULTURE SYSTEM

(71) Applicants: Public University Corporation Yokohama City University, Kanagawa (JP); Biomedica Solution Co., Ltd., Ibaraki-shi, Osaka (JP); SHIBUYA CORPORATION, Ishikawa (JP)

(72) Inventors: Hideki Taniguchi, Kanagawa (JP); Takanori Takebe, Kanagawa (JP); Keisuke Sekine, Kanagawa (JP); Atsushi Nakao, Osaka (JP); Takashi Hiromatsu, Osaka (JP); Hironobu Sunayama, Ishikawa (JP); Tetsuya Nishimura, Ishikawa (JP)

(73) Assignees: PUBLIC UNIVERSITY CORPORATION YOKOHAMA CITY UNIVERSITY, Kanagawa (JP); BIOMEDICA SOLUTIONS CO., LTD., Osaka (JP); SHIBUYA CORPORATION, Ishikawa (JP)

( * ) Notice: Subject to any disclaimer, the term of this patent is extended or adjusted under 35 U.S.C. 154(b) by 0 days.

(21) Appl. No.: 15/513,442

(22) PCT Filed: Sep. 18, 2015

(86) PCT No.: PCT/JP2015/076615
§ 371 (c)(1),
(2) Date: Mar. 22, 2017

(87) PCT Pub. No.: WO2016/047571
PCT Pub. Date: Mar. 31, 2016

(65) Prior Publication Data
US 2017/0306285 A1    Oct. 26, 2017

(30) Foreign Application Priority Data
Sep. 26, 2014 (JP) .................................. 2014-197443

(51) Int. Cl.
C12M 1/26 (2006.01)
C12M 1/00 (2006.01)
C12M 1/12 (2006.01)

(52) U.S. Cl.
CPC ............ *C12M 37/00* (2013.01); *C12M 23/34* (2013.01); *C12M 33/00* (2013.01); *C12M 41/14* (2013.01)

(58) Field of Classification Search
CPC ...... C12M 23/34; C12M 33/00; C12M 37/00; C12M 41/14
(Continued)

(56) References Cited

U.S. PATENT DOCUMENTS

2004/0215362 A1*  10/2004  Kokubo .................. A61L 2/04
                                                          700/130
2005/0170491 A1*  8/2005  Takagi .................. C12M 37/00
                                                          435/287.1
(Continued)

FOREIGN PATENT DOCUMENTS

JP    2005-278565    10/2005
JP    2011-4613      1/2011
(Continued)

OTHER PUBLICATIONS

Nakao, "Cell Processing Isolator ni yoru GMP Kanri no Koritsuka", BIO Clinica, vol. 23, No. 9, 2008, pp. 69-75.
(Continued)

*Primary Examiner* — Liban M Hassan
(74) *Attorney, Agent, or Firm* — Greenblum & Bernstein, P.L.C.

(57) ABSTRACT

An operation isolator forms an aseptic space. An incubator is connected to the operation isolator, in which cells are stored and cultured. A storage chamber stores articles used in the operation isolator. In order to carry articles from the
(Continued)

outside into the storage chamber, a decontamination pass-box is provided. The storage chamber and the operation isolator are directly or indirectly connected to each other.

7 Claims, 4 Drawing Sheets

(58) Field of Classification Search
USPC .................................................. 435/289.1
See application file for complete search history.

(56) References Cited

U.S. PATENT DOCUMENTS

| | | |
|---|---|---|
| 2011/0212513 A1 | 9/2011 | Yokoi et al. |
| 2012/0077220 A1 | 3/2012 | Mizutani et al. |
| 2012/0273047 A1 | 11/2012 | Yokoi et al. |
| 2013/0126302 A1* | 5/2013 | Johns .................. B01D 21/262 198/439 |
| 2013/0130361 A1* | 5/2013 | Okano .................. C12M 23/44 435/286.1 |
| 2014/0289877 A1 | 9/2014 | Taniguchi et al. |

FOREIGN PATENT DOCUMENTS

| | | |
|---|---|---|
| JP | 2011-177091 | 9/2011 |
| JP | 2012-231726 | 11/2012 |
| JP | 2013-135858 | 7/2013 |
| WO | 2004/114378 | 12/2004 |
| WO | 2013/047639 | 4/2013 |
| WO | 2016/183513 | 11/2016 |

OTHER PUBLICATIONS

Search Report issued in International Bureau of WIPO Patent Application No. PCT/JP2015/076615, dated Dec. 28, 2015.
Masahiro Kino-Oka, "Facilities and Cellculture Apparatus for Regenerative Medicine", The Japanese Society for Regenerative Medicine, Nov. 1, 2012, pp. 361-366.
Office Action issued in Japan Counterpart Patent Appl. No. 2014-197443, dated Aug. 28, 2018.
Biospherix, Ltd., "BioSpherix, cell research products", Biospherix, cell research products, Apr. 24, 2018, pp. 1-25.
Biospherix, Ltd., "Xvivo system, Xvivo System Modules, Xvivo System Configurations", Biospherix Cytocentric Cell Incubation & Processing Systems, Feb. 15, 2014, pp. 1-4,1-3,1-3.
Office Action issued in European Patent Office (EPO) Counterpart Patent Appl. No. 15843860.6, dated May 8, 2018.

* cited by examiner

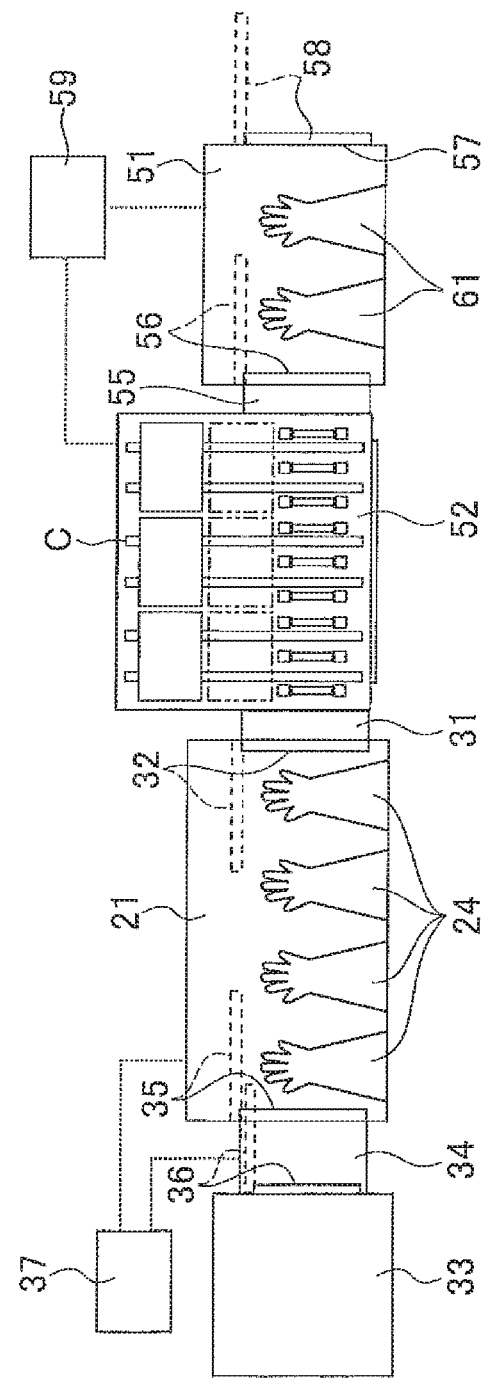

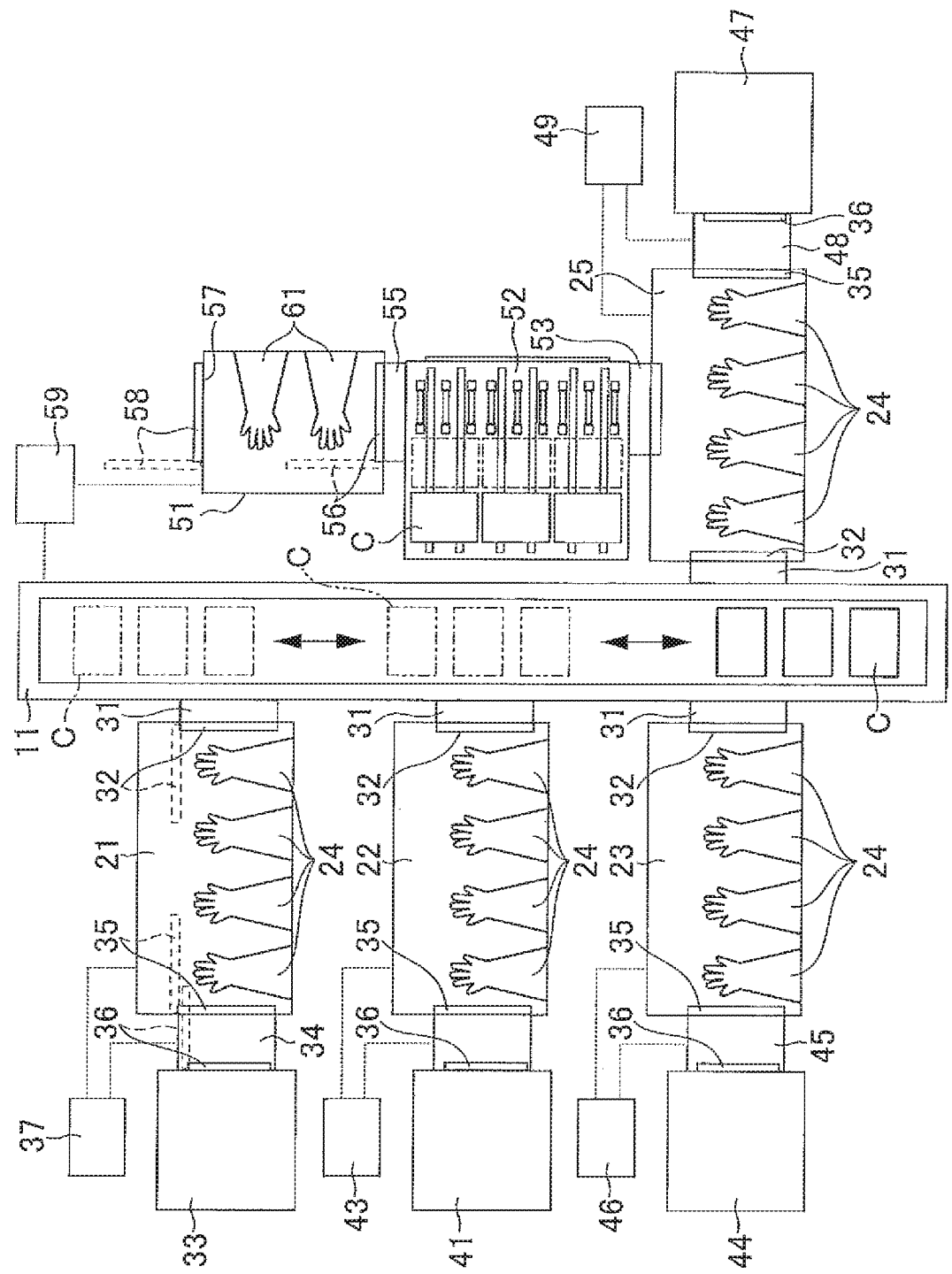

CELL CULTURE SYSTEM

TECHNICAL FIELD

The present invention relates to a cell culture system used in a regenerative medicine, in which damaged biofunctions are rejuvenated using stem cells, and particularly relates to a cell culture system, in which an incubator for storing and culturing cells is connected to an operation isolator for preparing cells.

BACKGROUND ART

As disclosed in PATENT DOCUMENT 1, an organ cell obtained from a multifunctional stem cell such as an iPS cell, a vascular endothelial cell forming a vascular endothelium, or a mesenchymal cell forming a support structure for a cell functioning in tissue is cultured. A co-culture is then performed with the optimum mixture ratio so that a steric organ bud having a microvascular structure can be induced in a test tube and eventually transplanted into an organism to produce an organ.

In order to culture such cells or tissue, there is known a system, which comprises an isolator forming an aseptic space, and an incubator detachably connected to the isolator to store and culture cells, to perform necessary operations for culturing in the isolator. In a system disclosed in PATENT DOCUMENT 2, for example, two isolators connected to incubators are connected to each other through a sterilized chamber, so that different kinds of cells can be cultured in each of the incubators.

PATENT DOCUMENT 1: International Publication No. WO2013/047639A1
PATENT DOCUMENT 2: Japanese Unexamined Patent Publication No. 2013-135858

SUMMARY OF THE INVENTION

Problems to be Solved by the Invention

When culturing different cells and performing a co-culture, it is necessary to prepare each cell separately so that a cultured cell can be mixed with the other cell. This preparation is required to be promptly performed in a short amount of time. In a conventional system, however, many articles cannot be stored in the isolator, and thus for each cell, articles needed for culturing such as material, an apparatus, culture vessel and so on have to be subjected to sterilization as necessary, and transported from outside. Because of this, an operation necessary for culturing a cell cannot be performed effectively.

In the system disclosed in PATENT DOCUMENT 2, since two isolators are connected through the sterilized chamber, a preparation for different cells, which have been simultaneously cultured at the same time, can be performed. In this case, when the cells are transferred between the isolators, contamination by various germs from outside should not occur. The cells delivered from one isolator are transferred to the other isolator through the sterilized chamber, which should be sterilized for each transfer since the sterilized chamber has a portion exposed to the outside. Thus, it is difficult to perform the preparatory operation in the isolator within a short amount of time.

The object of the present invention is to provide a cell culture system, by which an operation needed to culture cells in the operation isolator can be performed effectively and promptly in a short amount of time while cells being treated are not contaminated by various germs.

Means for Solving the Problems

A cell culture system of the present invention, which has an operation isolator forming an aseptic space and an incubator connected to the operation isolator for storing and culturing cells, comprises a storage chamber for storing an article, which is used in the operation isolator, and a pass-box through the article is transferred from the outside into the storage chamber, the storage chamber and the operation isolator being directly or indirectly connected to each other.

The cell culture system may be provided with a transportation isolator, which is disposed with a transporting mechanism in an aseptic space therein, and a plurality of operation isolators and incubators may also be provided. In this case, it is preferable that the plurality of operation isolators is arranged along the transportation path and connected to the transportation isolator, and the storage chamber and the operation isolator are connected to each other through the transportation isolator. In such a structure, the cell culture system may further comprise a plurality of containers containing the article, the article being stored in the storage chamber and transported by the transporting mechanism in a state in which the article is contained in the container. The transportation path of the transportation isolator may be formed in a straight line, and the transporting mechanism may transport the container in a reciprocal manner.

Preferably, the storage chamber is detachably provided.

Further, different kinds of cells may be cultured in the plurality of incubators, and the cells cultured in the different incubators may be mixed in any one of the operation isolators. Alternately, the same kind of cells may be cultured in the plurality of incubators, and the cells cultured in the different incubators may be mixed in any one of the operation isolators.

Effects of the Invention

According to the present invention, an operation needed to culture cells in the operation isolator can be performed effectively and promptly in a short amount of time while treated cells are not contaminated by various germs.

BRIEF DESCRIPTION OF THE DRAWINGS

FIG. 4 A plan view showing the general structure of a cell culture system to which a second embodiment of the present invention is applied.

FIG. 5 A plan view showing the general structure of a cell culture system to which a third embodiment of the present invention is applied.

EXPLANATION OF REFERENCES

Figure 1:
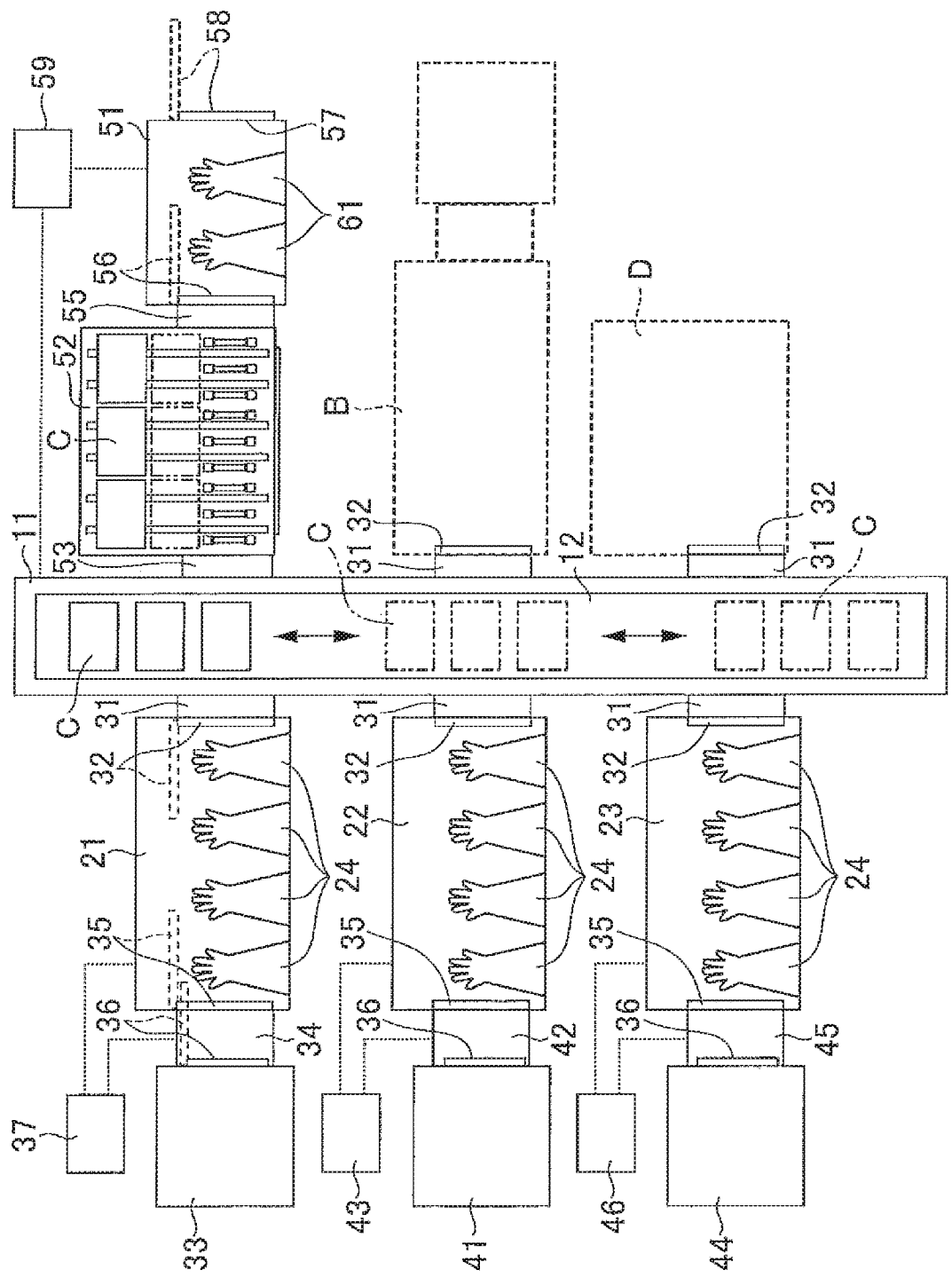
FIG. 1 A plan view showing the general structure of a cell culture system to which a first embodiment of the present invention is applied.

11 transportation isolator
21, 22, 23 operation isolator
33, 41, 44 incubator
51 decontamination pass-box
52 storage chamber

EMBODIMENT OF THE INVENTION

In the following, the present invention will be described with reference to embodiments shown in the drawings.

FIG. 1 shows the general structure of a cell culture system to which a first embodiment of the present invention is applied. A transportation isolator 11 is an elongated box-shaped casing extending directly upward and downward in FIG. 1. The inside of the transportation isolator 11 is maintained at a positive pressure, and is not in communication with the outside of the cell culture system to form an aseptic space. A belt conveyor (transporting mechanism) 12 is disposed in the transportation isolator 11. The belt conveyor 12, which is configured such that the transportation path is formed in a straight line along the longitudinal direction of the transportation isolator 11, reciprocally transports a cage C, which is a container containing an article. Articles such as material, an apparatus, culture vessel and so on, which are needed for culturing and are transported from outside of the cell culture system, are contained in the cage C. Thus, the first through third operation isolators 21-23 and a storage chamber 52, which are described later, are arranged along and connected to the linearly formed transportation path, and the belt conveyor 12 is moveable forwards and backwards, so that the cage C is promptly transported and the transportation speed is easily controlled when the transportation is automated. Further, since the transportation isolator 11 provided to cover the transportation path is formed in a simple elongated box-shape, decontamination of the inside space can be performed easily and with certainty without any blind spots. Note that the cage C may be directly mounted on the belt conveyor 12, or may be housed in a tray or the like.

In FIG. 1, first through third operation isolators 21-23 are arranged along the transportation path and connected to the left side of the transportation isolator 11. The first through third operation isolators 21-23 extend parallel to each other in a vertical direction with respect to the longitudinal direction. The inside of each of these operation isolators 21-23 is maintained at a positive pressure, and is not in communication with the outside of the cell culture system to form an aseptic space.

The first operation isolator 21 is provided with gloves 24 for opening and closing doors 32 and 35 described later, and for carrying out various operations. The first operation isolator 21 is connected to the transportation isolator 11 through an opening 31, which is opened and closed by a door 32. When the door 32 is closed, the first operation isolator 21 is shut off airtight from the transportation isolator 11. When the door 32 is open, a cage C can be transferred between the inside of the first operation isolator 21 and the inside of the transportation isolator 11.

An incubator 33 for storing and culturing cells is connected to the first operation isolator 21 through a connecting device 34. An opening provided on the connecting device 34 side of the first operation isolator 21 is opened and closed by a door 35, and the connecting device 34 is provided on an outer wall of the first operation isolator 21 to enclose the door 35. The first operation isolator 21 is shut off airtight from the inside space of the connecting device 34 by the door 35. An opening provided on the connecting device 34 side of the incubator 33 is opened and closed by a door 36, and the connecting device 34 is provided to enclose the periphery of the door 35. The inside of the incubator 33 is sealed airtight by the door 36. The incubator 33 can be separated from the first operation isolator 21 under the condition in which the doors 35 and 36 are closed.

A decontamination gas supply device 37, which supplies decontamination gas such as hydrogen peroxide vapor, for example, is connected to the first operation isolator 21 and the connecting device 34. That is, while the door 32 is closed and the doors 35 and 36 are open, the insides of the first operation isolator 21 and the incubator 33 are decontaminated. On the other hand, when the incubator 33 is attached or detached, the inside of the connecting device 34 is supplied with decontamination gas while the doors 35 and 36 are closed to perform a decontaminating operation for the exposed portions of the doors 35 and 36.

The second and third operation isolators 22 and 23 have similar structures as those of the first operation isolator 21. That is, an incubator 41 is connected to the second operation isolator 22 through a connecting device 42, and a decontamination gas supply device 43 is connected to the second operation isolator 22 and the connecting device 42. Similarly, an incubator 44 is connected to the third operation isolator 23 through a connecting device 45, and a decontamination gas supply device 46 is connected to the third operation isolator 23 and the connecting device 45. In FIG. 1, common references to the first operation isolator 21 are shown regarding the opening 31, doors 32, 35, and 36, and gloves 24.

A decontamination pass-box 51 is provided on the right side of the transportation isolator 11 in FIG. 1. The decontamination pass-box 51 is provided for transferring articles such as material, an apparatus, culture vessel and so on, which are needed for culturing cells, from the outside into the transportation isolator 11. That is, in the decontamination pass-box 51, the articles and the cage C are decontaminated, and the articles are then transferred into the cage C. Further, cells to be cultured are transferred through the decontamination pass-box 51.

The decontamination pass-box 51 is connected to the transportation isolator 11 through the storage chamber 52. That is, the storage chamber 52 is disposed between the decontamination pass-box 51 and the transportation isolator 11, and a cage C, in which an article is contained, is temporarily stored in the storage chamber 52. Gloves 61 for opening and closing a door 56 described later, and for carrying out various operations are provided for the decontamination pass-box 51.

The decontamination pass-box 51 and the storage chamber 52 are positioned facing the first operation isolator 21, and extend in a direction opposite to the first operation isolator 21. The storage chamber 52 is connected to the transportation isolator 11 through an opening 53, so that the cage C can be transferred between the inside of the storage chamber 52 and the inside of the transportation isolator 11. Due to this construction, the inside of the storage chamber 52 is maintained at a positive pressure to form an aseptic space similarly to the inside of the transportation isolator 11, and the storage chamber 52 and the first operation isolator 21 are indirectly connected to each other through the transportation isolator 11.

The decontamination pass-box 51 is connected to the storage chamber 52 through an opening 55, which is open and closed by the door 56. When the door 56 is closed, the decontamination pass-box 51 is shut off airtight from the storage chamber 52, and when the door 56 is open, the cage C can be transferred between the inside of the decontamination pass-box 51 and the inside of the storage chamber 52.

A transportation opening 57 is formed in a portion of the decontamination isolator 51 opposite to the storage chamber 52, and is opened and closed by a door 58. The door 58 is exposed to the outside of the cell culture system, and an article can be transferred in and out of the decontamination pass-box 51 by opening the door 58. When the door 58 is open, the door 56 is closed, and thus the storage chamber 52 and the transportation isolator 11 are not in communication with the outside. That is, the storage chamber 52 and the transportation isolator 11 form an aseptic space.

A decontamination device 59 is connected to the decontamination pass-box 51 and the transportation isolator 11. While the doors 56 and 58 are closed, the inside of the decontamination pass-box 51 and articles such as material, an apparatus, culture vessel and so on, which are transferred from the outside, are decontaminated. A decontaminating operation of the inside of the transportation isolator 11 is performed under the condition in which the door 32 and so on, which are provided between the transportation isolator 11 and the first through third operation isolators 21-23, are closed while the inside of the storage chamber 52 is decontaminated.

Figure 2:
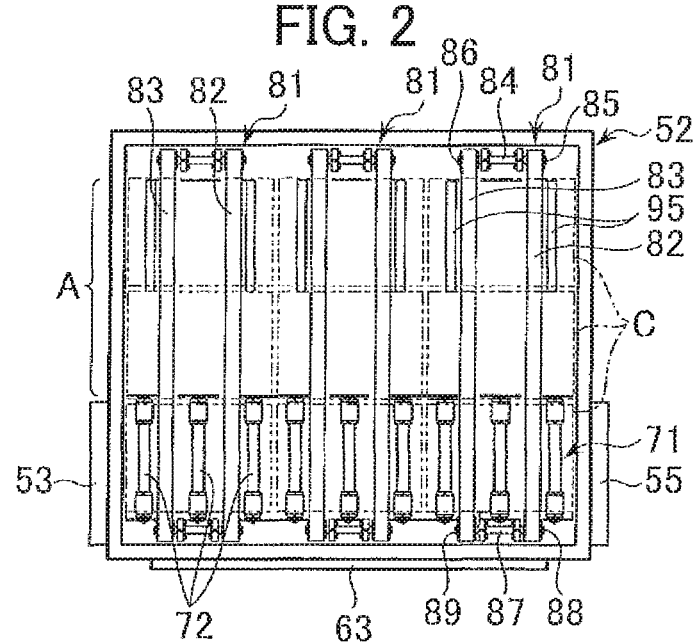
FIG. 2 A plan view showing the structure of the inside of a storage chamber.
Figure 3:
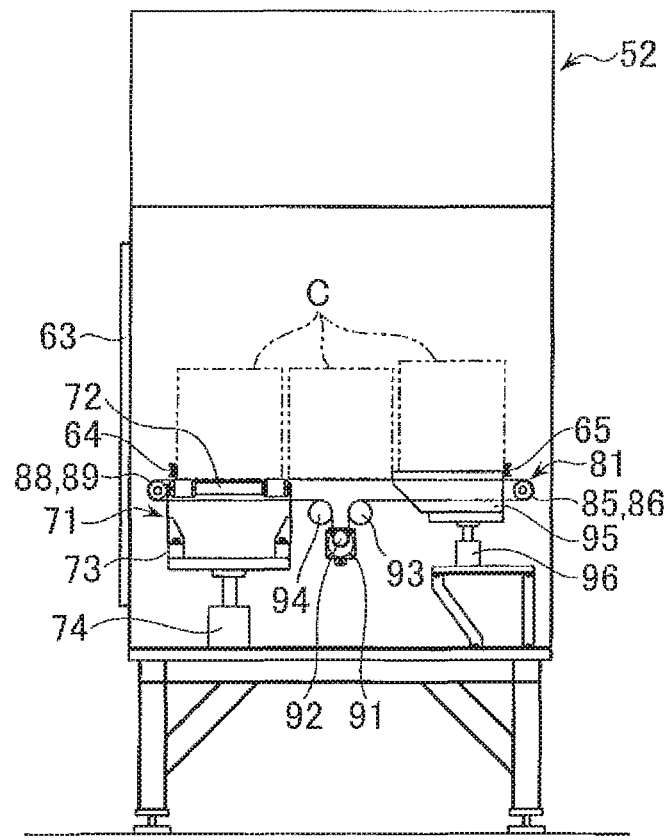
FIG. 3 A side view showing the structure of the inside of a storage chamber.

With reference to FIGS. 2 and 3, the construction of the storage chamber 52 is described.

The storage chamber 52 is provided with a motor roller conveyor 71 and three belt conveyors 81. The motor roller conveyor 71 is arranged on the side of a front window 63 to transport a cage C storing articles such as material, an apparatus, culture vessel and so on, which are needed for culturing cells, between the openings 53 and 55, i.e., right and left directions in FIG. 2. Each of the belt conveyors 81 transports the cage C in up and down directions perpendicular to the transporting direction of the motor roller conveyor 71, and transfers the cage C from the motor roller conveyor 71 to a storage area A, or transfers it from the storage area A to the motor roller conveyor 71.

The example of FIG. 2 is shown such that three cages C are mounted on the motor roller conveyor 71 and three cages C are mounted on each of the belt conveyors 81, but a maximum of six cages C can be mounted in the storage area A. That is, when six cages C are stored in the storage area A, there is no cage C on the motor roller conveyor 71. Note that the number of cages C which can be stored in the storage area A is merely one example, and the number of belt conveyors 81 is also merely one example. The numbers can be freely determined in accordance with the object.

The motor roller conveyor 71 has a plurality (nine in the drawing) of rollers 72, which are arranged in parallel to each other. Each of the rollers 72 is rotationally supported about the axis by a support mechanism 73, and is rotated in forward and reverse directions periodically by a drive mechanism not shown, and thus, a cage C is transported from the opening 55 to the opening 53 or in the opposite direction. The support mechanism 73 is driven up and down by a piston of an air cylinder 74, and each of the rollers 72 is set to either an up-position, at which the roller is projected above the conveying surface of the belt conveyors 81, or a down-position, at which the roller is depressed into the conveying surface of the belt conveyors 81. That is, the conveying surface of the motor roller conveyor 71 is set to the up-position when transporting the cage C, and is set to the down-position when not transporting the cage C.

The nine rollers 72 of the motor roller conveyor 71 can be driven or stopped in groups of three rollers. That is, in FIG. 2, the three rollers 72 positioned at the opening 55 side, the three rollers 72 positioned in the center, and the three rollers 72 positioned at the other opening 53 side are independently controlled from each other. For example, under the condition in which only the three rollers 72 on the opening 55 side are stopped, the six rollers 72 in the center and other opening 53 side can be driven.

Each of the belt conveyors 81 has the same structure with a pair of belts 82 and 83. These belts 82 and 83 are extended in the longitudinal direction of the rollers 72, and positioned between two adjacent rollers 72. One end of the belts 82 and 83 is wound around pulleys 85 and 86, which are provided at both ends of a support shaft 84, and the other end of the belts is wound around pulleys 88 and 89, which are provided at both ends of a support shaft 87. Between the support shafts 84 and 87, the belts 82 and 83 are wound around a drive shaft 92 of a drive motor 91 and idler pulleys 93 and 94, which are provided below the support shafts 84 and 87, and are rotated forwards and backwards by the drive motor 91, so that the cage C can be transported between the motor roller conveyor 71 and the storage area A.

A stopper 95 is provided on the opposite side of the belt conveyor 81 with respect to the motor roller conveyor 71, and on the outside of the pair of belts 82 and 83. The stopper 95 is driven to move up and down by a piston of an air cylinder 96, and rises and falls between an up-position, which is higher than the conveying surface of the belt conveyors 81, and a down-position, which is lower than the conveying surface. When the stopper 95 is in the up-position, the cage C supported by the stopper 95 is released upward from the belt conveyor 81 and the cage C, which is transported from the motor roller conveyor 71 side to the storage area A, comes into contact with the stopper 95 and stops.

As shown in FIG. 3, a first guide member 64 is provided at the end portion of the belt conveyor 81 closest to the front window 63 side of the motor roller conveyor 71. The first guide member 64 is arranged along the transporting direction of the motor roller conveyor 71, and extends from a portion close to the opening 53 to a portion close to the other opening 55. A second guide member 65, which extends in parallel to the first guide member 64, is provided at the end portion of the belt conveyor 81 opposite to the motor roller conveyor 71. A cage C can be engaged with the first and second guide members 64 and 65. The first guide member 64 guides the cage C when the cage C is transported by the motor roller conveyor 71, and functions as a stopper for the cage C at the end of the belt conveyor 81, which also applies to the second guide member 65.

The belt conveyor 12 of the transportation isolator 11, and the motor roller conveyor 71 and the belt conveyor 81 of the storage chamber 52 are driven by a manual operation of an operator turning on and off the electric power supply. The up and down movements of the motor roller conveyor 71 and stopper 95 are driven by a manual operation of an operator activating the air cylinders 74 and 96.

An operation of the embodiment is described below.

Prior to introducing a culture of cells, the insides of the decontamination pass-box 51, the storage chamber 52, the transportation isolator 11, the operation isolators 21, 22, and 23, and the incubators 33, 41, and 44 are decontaminated. Articles such as material, an apparatus, culture vessel and so on, which are needed for culturing cells, are carried in the decontamination pass-box 51, where the articles are decontaminated and stored in cages C. The motor roller conveyor 71 is set to the up-position, so that the cages C are carried into the storage chamber 52 one by one, and the maximum number of cages C that are mounted on the motor roller conveyors 71 is three.

In this state, if additional cages C are introduced from the decontamination pass-box 51, a cage C, which is not required to be immediately transferred to the operation isolator, is moved from the motor roller conveyor 71 to the storage area A. In this case, the motor roller conveyor 71 is lowered, and the cage C is moved by the belt conveyor 81. At this time, if there is no cage C at the position of the stopper 95 in the storage area A, the stopper 95 is set to the down-position, and the cage C is transported above the stopper 95 until it stops by coming into contact with the second guide member 65. Conversely, when the cage C is transported onto the stopper 95, as shown in FIG. 3, the stopper 95 is set to the up-position, so that the next cage C transported by the belt conveyor 81 stops when it comes into contact with the stopper 95.

When the cage C stored in the storage area A is transferred to the transportation isolator 11, the cage C is moved by the belt conveyor 81 until it stops when it comes into contact with the first guide member 64. The motor roller conveyor 71 is then moved upward to operate, and the cage C is carried to the transportation isolator 11 side. When the cage C positioned at the stopper 95 is moved to the motor roller conveyor 71, the stopper 95 is first set to the down-position, by which the cage C is mounted on the belt conveyor 81 and moved above the motor roller conveyor 71.

The three cages C on the motor roller conveyor 71 are moved to the transportation isolator 11 and are transported to the first, second, and third operation isolators 21, 22, and 23 by the belt conveyor 12 of the transportation isolator 11. That is, although the first cage C is initially placed on the belt conveyor 12, the first cage C is immediately carried into the first operation isolator 21 and the second cage C is moved to the second operation isolator 22 by the belt conveyor 12 and carried into the second operation isolator 22. The third cage C is transported to the third operation isolator 23 by the belt conveyor 12 and carried into the third operation isolator 23. At this time, cages C, which store simultaneously cultured cells, can be carried into each of the operation isolators 21, 22, and 23.

In each of the operation isolators 21, 22, and 23, packaging for material, an apparatus and a culture vessel stored in the cages C is removed, and the cells are seeded in the culture vessel. In this embodiment, for example, organ cells obtained from human iPS cells are seeded in the operation isolator 21, vascular endothelial cells are seeded in the operation isolator 22, and mesenchymal cells are seeded in the operation isolator 23. These culture vessels are transferred into the incubators 33, 41, and 44, which are then separated from the operation isolators, and culturing is performed for a predetermined period of time. During the culturing period, the incubators 33, 41, and 44 connected to the operation isolators 21, 22, and 23 as necessary, to carry out a medium replacement or passage.

When the culturing of each of the cells is completed, the incubators 33, 41, and 44 are connected to the operation isolators 21, 22, and 23, and the culture vessels, in which these three kinds of cells are stored, are removed from the operation isolators 21, 22, and 23, using predetermined treatments for picking up the cells from the culture vessels. The picked-up cells are stored in a special container, and then stored in cages C, which are transferred to the transportation isolator 11 and collected in either one of the different operation isolators 21, 22, and 23 by the belt conveyor 12. The three kinds of cells are mixed with each other at a predetermined mixture ratio in the operation isolator where the cells are collected. The culture vessel storing the mixed cells is transferred to the incubator to which the operation isolator is connected, and for a predetermined period of time, a co-culture is performed in the incubator which is separated from the operation isolator, such that a primordium of human liver is created. The cells, for which the co-culture is completed, are taken out of the incubator and placed in the operation isolator connected to the incubator. In the operation isolator, the cells are then subjected to a predetermined treatment, in which the cells are picked up from the culture vessel and stored in a special container. The container is then transported in the transportation isolator 11 and the storage chamber 52 to the outside through the decontamination pass-box 51. Note that the mixed cells are not necessarily different kinds of cells, but may be the same kind of cells separately cultured and then mixed together. Further, it is not necessary to co-culture cells after mixing, because the cells may be transported outside in the mixed state.

In the embodiment as described above, the cells cultured in the incubators 33, 41, and 44 are transferred between the first through third operation isolators 21, 22, and 23 through the transportation isolator 11. The transportation isolator 11 forms an aseptic space, which is not required to be decontaminated every time the transfer of cells between the operation isolators 21, 22, and 23 is performed. Therefore, operations using a plurality of incubators, which are required for a culture of cells, can be promptly carried out in a short amount of time, without mixing various germs in treated cells.

In the embodiment described above, although the first through third operation isolators 21, 22, and 23 and the incubators 33, 41, and 44 are provided, these components can be added and connected to the transportation isolator 11, as indicated by a broken line B in FIG. 1. In preparation for such addition, the opening 31 and the door 32 may be provided beforehand as shown by a solid line. Further, the storage chamber 52 and the decontamination pass-box 51 may be connected to the opening 31 as shown in a broken line D, and the decontamination pass-box 51 may be provided for a specific use such as carrying an article out of the system. Furthermore, the operation isolator, the storage chamber, and the decontamination pass-box may be detachably provided, so that they can be increased or decreased as necessary.

Although the storage chamber 52 in the embodiment is configured to dispose six cages C on a plane for storing them in the storage area A, it is possible to provide the storage spaces vertically in a multistage structure, such that a plurality of cages C is sterically arranged and stored. In this case, an elevator, which moves a cage C up and down in the storage spaces, is provided between the openings 53 and 55, and a moving mechanism composed of a motor roller conveyor, belt conveyor, and so on, which moves the cage C between the elevator and the openings 53 and 55, and moves the cages C between the elevator and each storage space, is provided. Further, the belt conveyor 12 is not necessarily formed along a straight line, but may have a curved portion or may be formed in a circular shape, in accordance with the layout of the installation site. Furthermore, keeping the cage C on the belt conveyor 12, articles such as material, an apparatus, culture vessel and so on, which are needed for culturing cells, can be temporarily stored in the transportation isolator 11. As the moving mechanism, a device other than the belt conveyor 12 can be adopted, which transports a cage C or tray while mounted on the mechanism, such as a rod-less cylinder, an electric linear actuator, or a linear motor car or vehicle moving along a guide rail. A device that transports a cage C or tray while holding it, such as a robot and so on, can also be adopted. Note that the structure of the moving mechanism should be as simple as possible, since decontamination becomes difficult if the structure of the moving mechanism is complex.

FIG. 4 shows a general structure of a cell culture system to which a second embodiment of the present invention is applied. The difference from the first embodiment is the direct connection between the storage chamber 52 and the first operation isolator 21. In the second embodiment, the storage chamber 52 and the first operation isolator 21 are connected through the opening 31, which is opened and closed by the door 32, so that a cage C can be transferred between the inside of the storage chamber 52 and the inside of the first isolator 21. The decontamination pass-box 51 is connected to the storage chamber 52 through the opening 55, which is similar to the first embodiment, and the decontamination gas supply device 59 is connected to the decontamination pass-box 51 and the storage chamber 52. The other structures are identical to the first embodiment, and the same references are assigned.

In the second embodiment described above, a plurality of incubators 33 are prepared, and can be connected to or detached from the first operation isolator 21, so that a preparation for cells can be performed in the first operation isolator 21, and the same or different kind of cells can be cultured in each of the incubators 33. The cultured cells are sequentially prepared and mixed with each other in the first operation isolator 21, and stored and co-cultured in any one of the incubators 33 connected thereto. In this case, articles such as material, an apparatus, culture vessel and so on, which are needed for the culturing of cells performed in the first operation isolator 21, have already been carried into the storage chamber 52 and stored there by the time they are to be used, and thus they can be carried in and used in the first operation isolator 21 as necessary. Especially, since the decontamination pass box 51 is connected to the storage chamber 52 and the decontamination pass box 51 and the storage chamber 52 can be isolated by the door 32, articles such as material, an apparatus, culture vessel and so on can be sequentially carried into the decontamination pass-box 51 from the outside, decontaminated therein, and contained in cages C and stored in the storage chamber 52, while a preparation is performed in the first operation isolator 21 under the condition in which the first operation isolator 21 and the storage chamber 52 are isolated. In the second embodiment, similar to the first embodiment, an operation required for culturing cells can be effectively performed.

In a third embodiment shown in FIG. 5, the first operation isolator 21 connected to the storage chamber 52 in the second embodiment is connected to the transportation isolator 11, as a fourth operation isolator 25. The structure of the fourth operation isolator 25 is similar to those of the first through third operation isolators 21-23. That is, an incubator 47 is connected to the fourth operation isolator 25 through a connecting device 48, and a decontamination gas supply device 49 is connected to the fourth operation isolator 25 and the connecting device 48. In FIG. 5, regarding the opening 31, the doors 32, 35, and 36, and gloves 24, the common references to the first through third operation isolators 21-23 are assigned, and the fourth operation isolator 25 is connected to the transportation isolator 11 through the opening 31.

The storage chamber 52 is connected to the fourth operation isolator 25 through the opening 53, which is similar to the connection to the transportation isolator 11, so that a cage C can be transferred between the inside of the storage chamber 52 and the inside of the fourth operation isolator 25. Further, the decontamination pass-box 51 is connected to the storage chamber 52 through the opening 55 and the decontamination gas supply device 59 is connected to the decontamination pass-box 51 and the transportation isolator 11, which is similar to the first embodiment.

According to such a structure, the fourth operation isolator 25 is directly connected to the storage chamber 52, and the first through third operation isolators 21-23 are indirectly connected to the storage chamber 52 through the fourth operation isolator 25 and the transportation isolator 11.

In the third embodiment described above, in a similar way as the first embodiment, articles such as material, an apparatus, culture vessel and so on, which are needed for culturing cells, are carried into and decontaminated in the decontamination pass-box, contained in a cage C and stored in the storage chamber 52. For carrying the cages C in the first through third operation isolators 21-23, the cages C are transferred from the storage chamber 52 to the fourth operation chamber 25, and transported to each of the operation isolators 21, 22, and 23 through the transportation isolator 11. Further, it is possible that, in the fourth operation isolator 25, the cells are seeded in a culture vessel using material, an apparatus, culture vessel and so on housed in the cage C, and stored in the incubator 47 to culture. According to the third embodiment described above, effects similar to those of the first embodiment can be obtained.

The invention claimed is:

1. A cell culture system having a plurality of operation isolators forming an aseptic space, and a plurality of incubators connected to the plurality of operation isolators, the plurality of incubators configured to store and culture cells, the cell culture system comprising:

a storage chamber configured to store a plurality of containers, each of the plurality of containers containing an article which is used in the plurality of operation isolators, and a pass-box connected to the storage chamber, through which the article contained in each of the plurality of containers is transferable from an outside of the cell culture system into the storage chamber;

the storage chamber and the plurality of operation isolators being connected to each other, wherein the plurality of operation isolators is provided between the storage chamber and the plurality of incubators;

a transportation isolator, which is disposed with a conveyor in an aseptic space therein;

the plurality of operation isolators being arranged along a transportation path, wherein each of the plurality of operation isolators is connected to the transportation isolator via a respective separate opening having a corresponding door, and wherein the storage chamber and the plurality of operation isolators are connected to each other through the transportation isolator;

wherein an end of each of the plurality of incubators is coupled to an end of a corresponding operation isolator of the plurality of operation isolators; and wherein the conveyor is configured to transport the article stored in the storage chamber, in a state in which the article is contained in a respective one of the plurality of containers.

2. The cell culture system according to claim 1, wherein the transportation path of the transportation isolator is formed in a straight line, and the conveyor transports the plurality of containers in a reciprocal manner.

3. The cell culture system according to claim 1, wherein the storage chamber is detachably provided.

4. The cell culture system according to claim 1, wherein the plurality of incubators are configured to have different kinds of cells cultured therein such that the cells cultured in different ones of the plurality of incubators are mixable in any one of the plurality of operation isolators.

5. The cell culture system according to claim 1, wherein the plurality of incubators are configured to have same kinds of cells cultured therein such that the cells cultured in different ones of the plurality of incubators are mixable in any one of the plurality of operation isolators.

6. The cell culture system according to claim 1, wherein the storage chamber is detachably provided.

7. The cell culture system according to claim 1, wherein the conveyor is a belt conveyor.

\* \* \* \* \*

UNITED STATES PATENT AND TRADEMARK OFFICE
CERTIFICATE OF CORRECTION

PATENT NO. : 10,647,955 B2
APPLICATION NO. : 15/513442
DATED : May 12, 2020
INVENTOR(S) : Hideki Taniguchi et al.

It is certified that error appears in the above-identified patent and that said Letters Patent is hereby corrected as shown below:

On the Title Page

(73) Assignees, please change:
"PUBLIC UNIVERSITY CORPORATION YOKOHAMA CITY UNIVERSITY, Kanagawa (JP); BIOMEDICA SOLUTIONS CO., LTD., Osaka (JP); SHIBUYA CORPORATION, Ishikawa (JP)"
To:
-- PUBLIC UNIVERSITY CORPORATION YOKOHAMA CITY UNIVERSITY, Kanagawa (JP); BIOMEDICA SOLUTION CO., LTD., Osaka (JP); SHIBUYA CORPORATION, Ishikawa (JP) --

Signed and Sealed this
Twenty-eighth Day of July, 2020

Andrei Iancu
*Director of the United States Patent and Trademark Office*